United States Patent

Dabir et al.

[11] Patent Number: 5,891,164
[45] Date of Patent: *Apr. 6, 1999

[54] SURGICAL NEEDLE

[76] Inventors: Reza Dabir, 742 Sheldon Rd., Grosse Pointe Shores, Mich. 48236; George Trutza, 159 College Park Dr., Fairfield, Conn. 06430

[*] Notice: This patent issued on a continued prosecution application filed under 37 CFR 1.53(d), and is subject to the twenty year patent term provisions of 35 U.S.C. 154(a)(2).

[21] Appl. No.: 763,503

[22] Filed: Dec. 11, 1996

[51] Int. Cl.⁶ ..................................................... A61B 17/04
[52] U.S. Cl. ............................ 606/222; 606/223; 606/224
[58] Field of Search .................................. 606/222, 223, 606/224

[56] References Cited

U.S. PATENT DOCUMENTS

| | | | |
|---|---|---|---|
| 527,263 | 10/1894 | Blanchard . | |
| 2,811,157 | 10/1957 | Kurtz et al. | 128/339 |
| 2,811,971 | 11/1957 | Scott . | |
| 3,608,095 | 9/1971 | Barry | 3/1 |
| 4,373,530 | 2/1983 | Kilejian | 606/145 |
| 4,524,771 | 6/1985 | McGregor et al. | 128/339 |
| 4,760,848 | 8/1988 | Hasson | 128/340 |
| 5,059,207 | 10/1991 | Shah | 606/223 |
| 5,222,962 | 6/1993 | Burkhart | 606/148 |
| 5,433,728 | 7/1995 | Kim | 606/223 |

FOREIGN PATENT DOCUMENTS

| | | |
|---|---|---|
| 0494644 | 1/1992 | European Pat. Off. . |
| 180378 | of 0000 | Germany . |
| 4114204 | 11/1992 | Germany . |
| 1572613 | 6/1990 | Russian Federation . |
| 876354 | 8/1961 | United Kingdom . |

OTHER PUBLICATIONS

Atlas of Vascular Surgery Basic Techniques and Exposures, Robert B. Rutherford, M.D. 1993.

*Primary Examiner*—Gary Jackson

[57] ABSTRACT

A surgical suturing needle is disclosed for use in limited space applications as well as a method for its use. The needle has an arcuate body and a relatively straight shank extending therefrom. The shank and arcuate body form an abrupt angle therebetween. The surgical suturing needle has a pointed tip on one end of the arcuate body and suture attachment structure formed in the shank. The method of using the surgical needle to join a pair of vascular tissue sections together includes penetrating into a lumen of a first vascular tissue section, advancing the pointed tip into the lumen of a second vascular tissue section and out through a side wall thereof, grasping the pointed tip and drawing the needle substantially parallel to an outer surface of the second vascular tissue section to thereby move the surgical suturing needle and an attached length of suture material through the first and second vascular tissue sections.

11 Claims, 4 Drawing Sheets

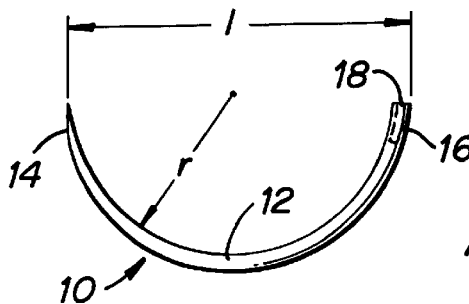
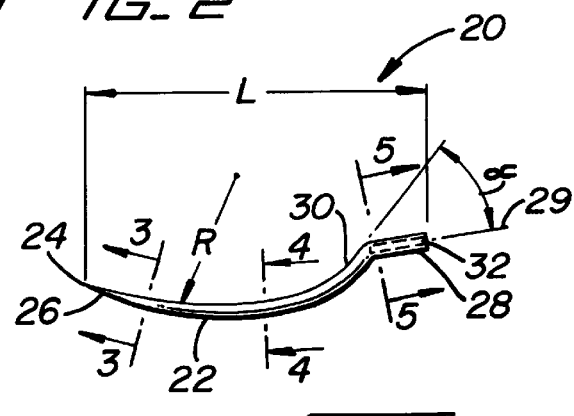
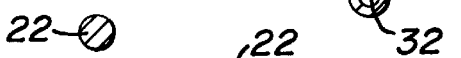
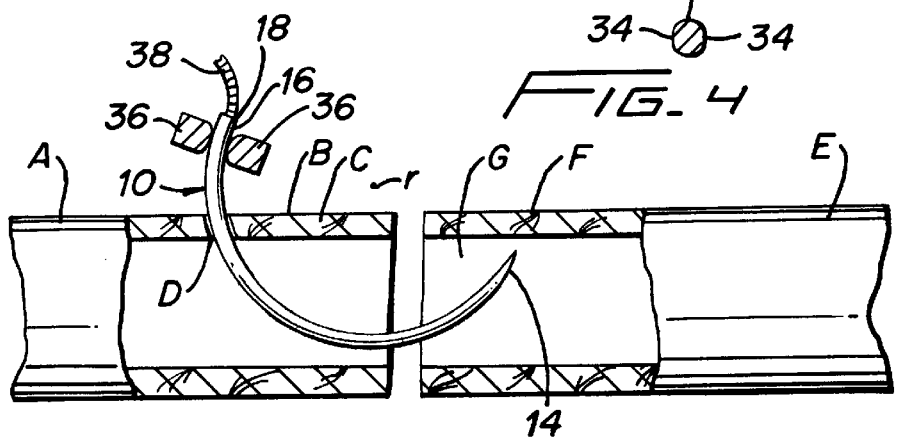
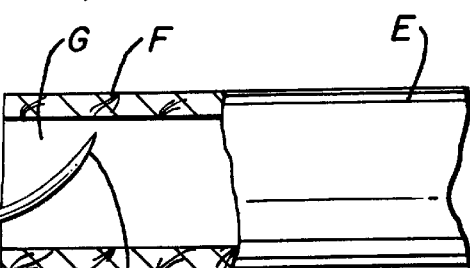
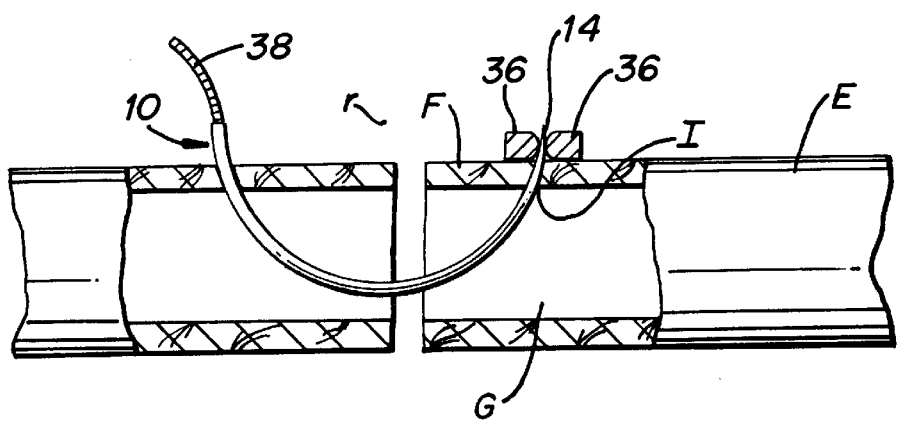

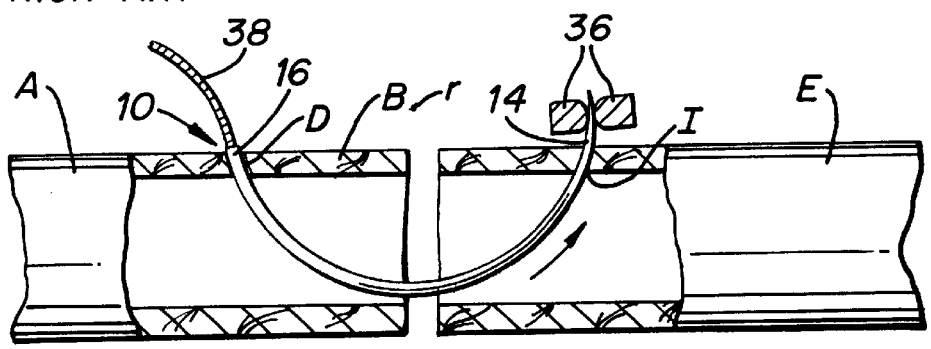
FIG_8 PRIOR ART
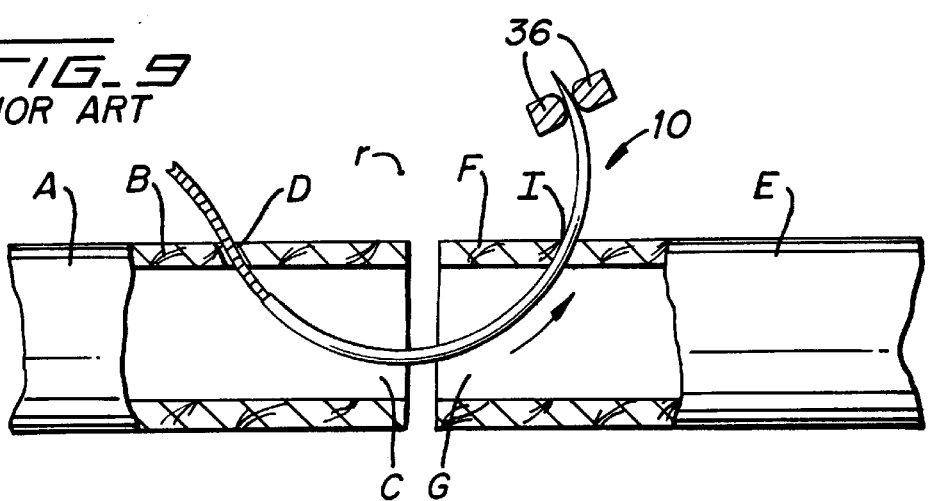
FIG_9 PRIOR ART
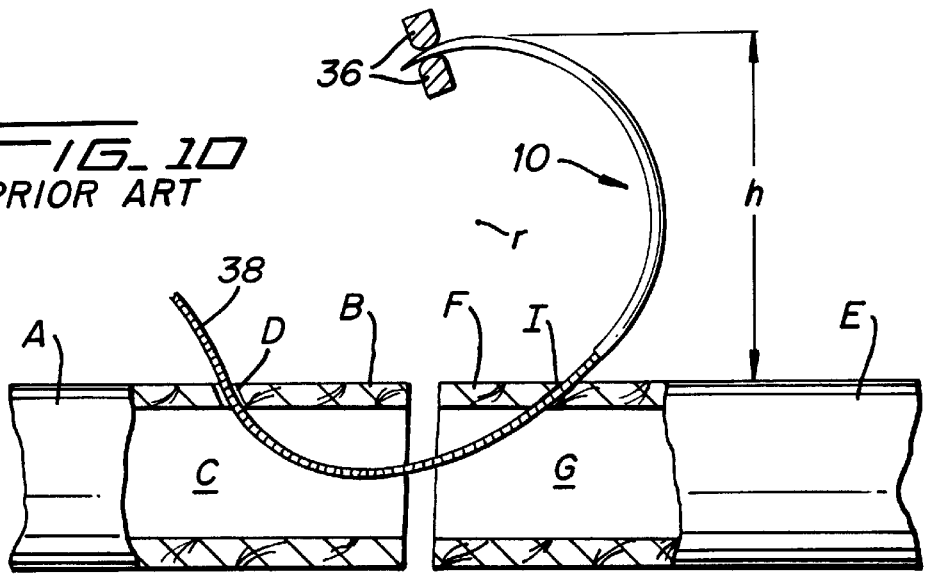
FIG_10 PRIOR ART

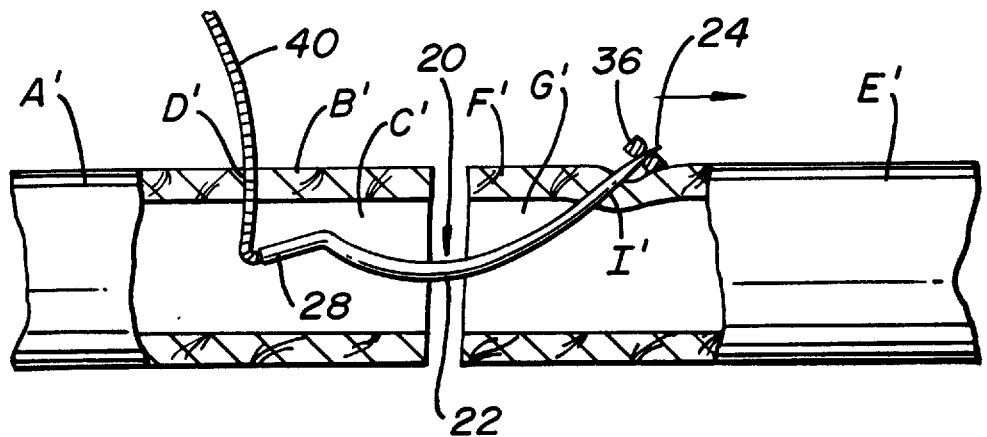
FIG_14
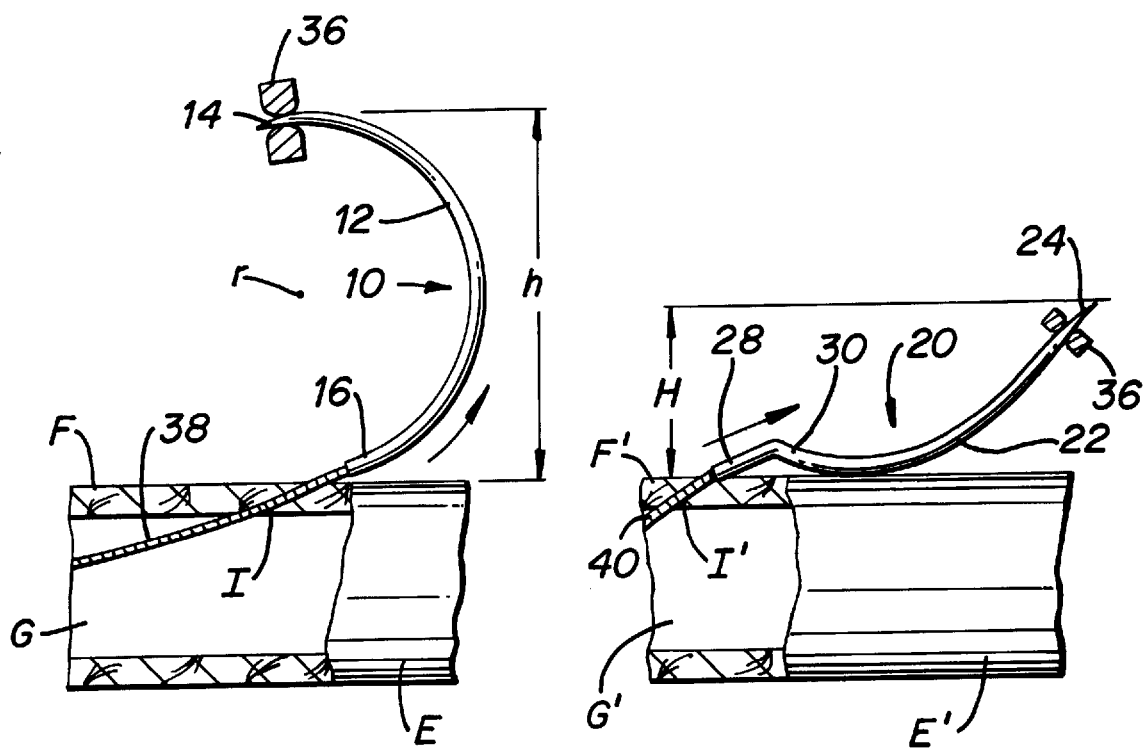
FIG_16 PRIOR ART
FIG_15

SURGICAL NEEDLE

BACKGROUND

1. Technical Field

This disclosure relates generally to surgical needles and methods of suturing and, more particularly, to a surgical needle and method of use particularly suited for use in limited space applications, such as, cardiovascular or microvascular surgery.

2. Description of Related Art

Various shapes and styles of surgical needles have been developed for use with specific suturing procedures. The needle configurations may vary according to the type of tissue to be sutured and the manner of manipulating the needle during suturing. For example, one such needle, used for suturing deep facia tissue, is disclosed in U.S. Pat. No. 5,433,728 to Kim ("Kim"). The Kim needle has an arcuate body with a pointed tip. The body forms an arc of approximately 180° to 230° and is joined to a relatively straight shank by a gently curving arcuate neck.

Another specific needle configuration is disclosed in European Patent Application No. 0494644 A2 ("EPO '644) The EPO '644 needle is disclosed for use in abdominal surgery and one embodiment includes a straight section which bends downwardly at approximately 22° and then curves upwardly with a radius of 5/12ths of the needle's overall length.

In certain surgical procedures, for example, cardiovascular or microvascular surgery, it is often necessary to join two hollow organ or vascular tissue sections together. This is most often accomplished by suturing opposing edges of the vascular tissue sections together. The type of surgical suturing needle used during these procedures typically is a needle having an arcuate shape of a substantially constant radius. Most often the arc of the needle encompasses having a pointed tip at one end and a tail portion at an opposite end which is drilled to retain an end of a length of suture material therein.

In order to suture two opposing vascular tissue sections together with prior art microvascular or cardiovascular surgical needles of the type described above, the suturing needle is typically held at its tail portion by a needle holder and rotated about the center of its radius through the tissue sections to be joined. For example, in order to suture two vascular tissue sections together, the two vascular tissue sections are approximated and the surgical needle having a length of suture attached thereto is rotated to cause the pointed tip to pierce through an outer wall of a first vascular tissue section and into its lumen. The needle is then rotated further to move the pointed tip of the needle through a lumen of the second vascular tissue section and out through an outer wall of the second vascular tissue section. Once the pointed tip has penetrated through the wall of the second vascular tissue section, the pointed tip is grasped with a needle holder and the tail portion is released.

In order to draw the length of suture through the two vascular tissue sections and remove the needle from the vascular tissue sections, it is necessary to continue to rotate the surgical needle further in approximately a half circle drawing the suture material through the tissue sections. During rotation of the needle through the vascular tissue sections, the force of the tail portion against the initial entrance hole in the first vascular tissue section may cause the entrance hole to become traumatized or enlarged. Since during the entire surgical procedure the needle must be rotated through approximately a complete circle, an operating space having a height more than half of the radius of the needle must be available adjacent the accessed vascular tissue sections.

In certain specific procedures, such as cardiovascular or microvascular surgical procedures, a very limited amount of space adjacent the accessed tissue sections is available for manipulation of the surgical needle. This is especially true when suturing behind the aorta. The proximity of tissue walls to the vascular tissue sections inhibits the surgeon's ability to substantially rotate a conventional surgical needle when suturing these tissues. Thus, there exists a need for a cardiovascular and/or microvascular surgical suturing needle configured to be manipulated within a limited space and with minimal trauma to the tissue sections to be sutured.

SUMMARY

There is disclosed a surgical needle which is particularly suited for use in limited space applications and a method for its use. The surgical needle includes an arcuate body having a pointed tip at one end. At an opposite end of the arcuate body there is provided a relatively short, straight shank which extends from the arcuate body at a predetermined angle. The predetermined angle is defined by the intersection of the arcuate body and the shank. In a preferred embodiment, this predetermined angle is preferably within a range of about 30° to 70°, with approximately 45° representing an optimum configuration. Preferably, an extrapolation of the longitudinal axis of the shank does not intersect any other portion of the surgical needle.

The arcuate body may have either a varying or a constant radius of curvature and preferably has a varying radius of curvature which increases progressively from the juncture with the shank toward the pointed tip. The surgical needle generally has a circular cross-section, however, in a preferred embodiment, a portion of the arcuate body may be formed with flat sides. Other cross-sectional configurations are also applicable and are contemplated by this disclosure. Suture attachment structure in the form of a counter sunk bore is provided in the shank. A suture may be attached thereto using any number of various known techniques, such as, for example, crimping, medical grade adhesives, etc.

A method of using the surgical needle is also disclosed. The method includes initially grasping the shank of the surgical needle with a needle holder. The pointed tip of the surgical needle is then forced against the wall of the first tissue section and driven into the lumen. The surgical needle is then manipulated to advance the pointed tip and arcuate body through the first lumen into a second lumen of the second vascular tissue section. The point ed tip is manipulated to penetrate the wall of the second vascular tissue section and protrude from an outer wall thereof. The pointed tip of the surgical needle is grasped with a needle holder and the shank is released. The surgical needle is then pulled substantially parallel to an outer surface of the second vascular tissue section to thereby draw the surgical needle through the entrance hole and out the exit hole to thereby form a stitch.

BRIEF DESCRIPTION OF THE DRAWING

Various embodiments are described hereinbelow with reference to the drawings, wherein:

FIG. 1 is a perspective view of a prior art surgical needle;

FIG. 2 is a perspective view of one embodiment of the present surgical needle;

FIG. 3 is a cross-sectional view taken along line 3—3 of FIG. 2;

FIG. 4 is a cross-sectional view taken along line 4—4 of FIG. 2;

FIG. 5 is a cross-sectional view taken along line 5—5 of FIG. 2;

FIG. 6 is a perspective view, partially shown in section, of the prior art needle of FIG. 1 initially penetrating a first vascular tissue section;

FIG. 7 is a view similar to FIG. 6 illustrating the prior art needle after penetrating a second vascular tissue section;

FIG. 8 is a view similar to FIG. 7 illustrating the prior art needle being drawn through the tissue sections;

FIG. 9 is a view similar to FIG. 8 illustrating the prior art needle after it has been drawn through the first vascular tissue section;

FIG. 10 is a view similar to FIG. 9 illustrating the prior art needle after it has been drawn through the second vascular tissue section;

FIG. 14 is a view similar to FIG. 13 illustrating the surgical needle of FIG. 2 being drawn completely through the first vascular tissue section;

FIG. 15 is a view similar to FIG. 14 illustrating the surgical needle of FIG. 2 being drawn out through the second vascular tissue section; and FIG. 16 is a partial view of the prior art view of FIG. 10 showing removal of the prior art suturing needle from a tissue section.

DETAILED DESCRIPTION OF PREFERRED EMBODIMENTS

Figure 11:
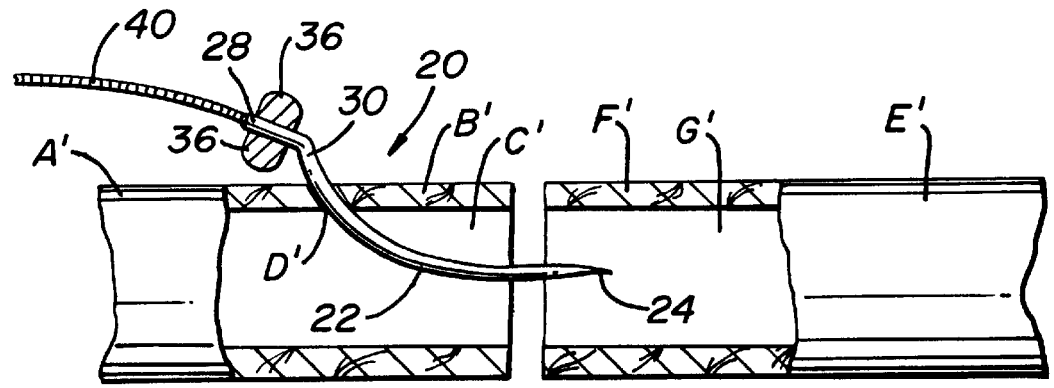
FIG. 11 is a perspective view, partially shown in section, illustrating the surgical needle of FIG. 2 penetrating a first vascular tissue section.

Referring initially to FIG. 1, there is shown a prior art surgical suturing needle 10 of the type typically used in cardiovascular or microvascular surgery. Needle 10 generally includes an arcuate body 12 typically having a constant radius of curvature "r". A pointed tip 14 is formed on one end of arcuate body 12 and a tail portion 16 is formed on an opposite end of arcuate body 12. Preferably, tail portion 16 includes a bore 18 for receipt of an end of a length of suture material therein. When used in cardiovascular and microvascular applications, needle 10 generally has an overall length "1" on the order of approximately 0.200 to 2.000 inches preferably about 0.305 to about 0.365 inches and most preferably about 0.328 to about 0.338 inches and a radius on the order of about 0.1 to about 2.0 inches. While surgical needle 10 is illustrated as forming half a circle with constant radius r, prior art surgical needles are also available in styles forming greater or less than half of a circular arc, for example, three eights of a circular arc.

Referring now to FIG. 2, there is illustrated a preferred embodiment of surgical needle 20. Surgical needle 20 includes a generally arcuate body 22 having a variable radius "$R_v$" and a relatively straight shank 28 extending from arcuate body 22. A pointed tip 24 is formed at a first end 26 of arcuate body 22 and shank 28 is formed on a second end 30. Arcuate body 22 is preferably solid, however, other configurations are also contemplated, such as, for example, fully or partially hollow, channel-shaped, etc. Variable radius R is substantially larger than that used with known surgical suturing needles, such as prior art needle 10 above, and gives a generally more flat profile to arcuate body 22. As noted above, radius R preferably varies, increasing from the juncture with shank 28 to pointed tip 24. Shank 28 forms a relatively abrupt juncture angle a with second end 30 of arcuate body 22. As used herein the term "abrupt" indicates distinct transition as opposed to gradual melding of one portion into another. Preferably, juncture angle a is on the order of approximately 30° to 70°, and more preferably, approximately 45°. It should be noted that an extrapolation of the longitudinal axis 29 of shank 28 does not intersect any other portion, for example, arcuate body 22, of surgical needle 20. Radius R preferably ranges from about 0.100 to about 2.00 inches and surgical needle 20 generally has an overall length L of approximately 0.305 to 0.365 inches. Shank 28 preferably has a length of approximately 0.055 inches to 0.130 inches, and more preferably, 0.100 inches.

As noted above, arcuate body 22 has a relatively large and varying radius R. In addition, surgical needle 20 may have consistent or varying cross-sectional shapes. Referring now to FIG. 3, arcuate body 22 has a generally circular cross-section adjacent pointed tip 24. However, as shown in FIG. 4, a portion of arcuate body 22 may be imparted with relatively flat sides 34 to increase strength and facilitate use. Shank 28 also has a generally circular cross-section and, as shown in FIGS. 2 and 5, includes suture attachment structure in the form of a bore 32 formed within shank 28 for receipt of an end of a length of suture material therein. The end of the length of suture material may be secured within bore 32 by known attaching techniques, such as, for example, crimping or use of surgical grade adhesives such as, for example, cyanoacrylate glue, epoxy cements or other medically acceptable adhesives.

Referring now to FIGS. 6–10, a brief description of the method of suturing an opposed pair of vascular tissue sections utilizing the prior art surgical needle 10 will now be described. As noted hereinabove, suturing with surgical needle 10 typically requires that surgical needle 10 be rotated almost completely about its center of radius, thus necessitating a significant amount of operating space adjacent the vascular tissue sections to be sutured.

Referring initially to FIG. 6, in order to suture two vascular tissue sections together, the distal end of a first vascular tissue section A having a wall B defining a lumen C therein is approximated adjacent a distal end of a second vascular tissue section E having a wall F and defining a lumen G therein. The tail portion 16 of surgical needle 10 is grasped with a needle holder 36 to manipulate the surgical needle. Surgical needle 10 is provided with a length of suture material 38 affixed within suture bore 18. Pointed tip 14 is positioned adjacent wall B and driven therethrough by rotating surgical needle 10 about its center of radius r. As surgical needle 10 penetrates wall B it creates an entrance hole D in wall B. Surgical needle 10 is rotated such that it passes through lumen C and into lumen G in second vascular tissue section E.

Referring now to FIG. 7, once a portion of surgical needle 10 has entered lumen G of the second vascular tissue section E, surgical needle 10 is rotated further to penetrate wall F thereby causing an exit hole I to be created in wall F. Pointed tip 14 is then grasped with a second needle holder 36 and the tail portion 16 is released from the first needle holder 36. Thus, having penetrated through both first and second vascular tissue sections A and E, surgical needle 10 is ready to be withdrawn from vascular tissue sections A and E thereby drawing a length of suture material 38 through vascular tissue sections A and E to form a stitch.

In order to draw surgical needle 10 through vascular tissue sections A and E, needle 10 is rotated further about its center of radius to draw a length of suture material into lumen C. As shown in FIG. 8, upon rotating surgical needle 10, tail portion 16 may press against edges of entrance hole D thereby enlarging the entrance hole and causing trauma thereto. If this trauma is significant, separate and additional stitching procedures may be required to close the enlarged entrance hole and prevent leakage.

Referring now to FIGS. 9 and 10, surgical needle 10 is rotated still further to draw surgical needle 10 through lumens C and G, and out through exit hole I thereby drawing length of suture material 38 through entrance and exit holes D and I to suture or stitch vascular tissue sections A and E together. With particular reference to FIG. 10, it can be easily seen that as surgical needle 10 is rotated out of vascular tissue section E, surgical needle 10 requires a significant amount of space in order to be manipulated, the height of this space is indicated by height "h", adjacent the outer surface of the vascular walls B and F. Further, as indicated above in FIG. 6, initial penetration of the first vascular tissue section A also requires a significant amount of space adjacent the outer wall B.

Thus, the suturing of vascular tissues with the known prior art surgical suturing needles of the type shown as suturing needle 10 typically requires a significant amount of operating space adjacent the vascular tissue sections in order to properly manipulate surgical needle 10.

Referring now to FIGS. 11–14, the provision of surgical needle 20 permits vascular tissue to be sutured using significantly less operating space adjacent the vascular tissue sections being sutured. Referring initially to FIG. 11, surgical needle 20, attached to suture material 40, may be utilized to suture together two opposed vascular tissue sections such as, first vascular tissue section A' and second vascular tissue section E'. First vascular tissue section A' has an outer wall B' and defining a lumen C' therein and second vascular tissue section E' has an outer wall F' and defining a lumen G' therein.

Initially, surgical needle 20 is grasped adjacent its shank 28 by needle holder 36. Pointed tip 24 is positioned adjacent wall B' and moved through and into inner lumen C'. The larger radius of curvature of arcuate body 22 adjacent pointed tip 24 allows pointed tip 24 to be driven into wall B' without having to substantially rotate surgical needle 20. As surgical needle 20 is passed through wall B' it creates an entrance hole D'. Surgical needle 20 can then be manipulated to advance arcuate body 22 through entrance hole D' and to advance pointed tip 24 into lumen G' of second vascular tissue section E'. Surgical needle 20 is then manipulated to cause pointed tip 24 to penetrate wall F' to create an exit hole I'. The smaller radius of curvature adjacent shank 28 facilitates driving pointed tip 24 through wall F' with a minimal amount of rotational motion. Shank 28 is thus positioned flush with or parallel to an outer surface of first vascular tissue section A'.

Figure 12:
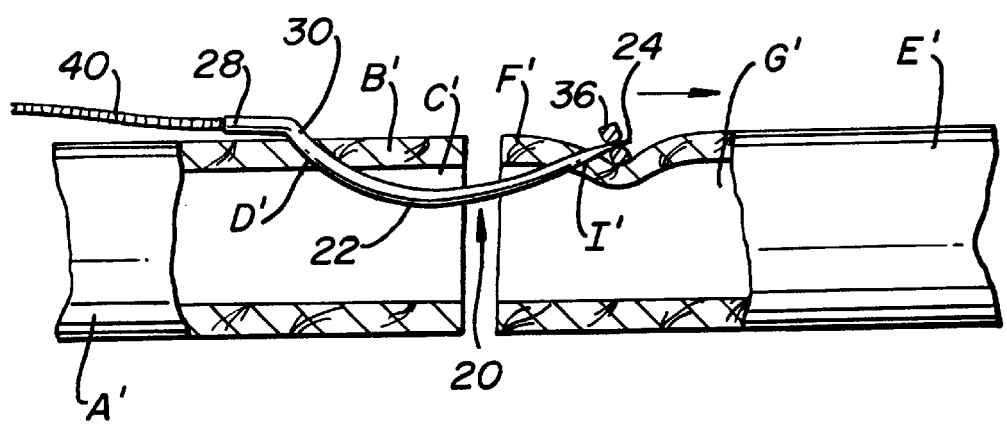
FIG. 12 is a view similar to FIG. 11 illustrating the surgical needle of FIG. 2 penetrating a second vascular tissue section.

Referring to FIG. 12, once pointed tip 24 has penetrated wall F' thereby creating exit hole I', shank 28 is released from the grasp of needle holder 36 and pointed tip 24 is grasped. In contrast to the rotational motion used to move prior art surgical needle 10 through the vascular tissue sections, surgical needle 20 is configured to be moved substantially parallel to a longitudinal axis of the vascular tissue sections. As shown in FIGS. 11 and 12, this motion of moving surgical needle 20 parallel to the longitudinal axis of the vascular tissue sections requires a significantly smaller amount of operating space adjacent the vascular tissue sections.

Figure 13:
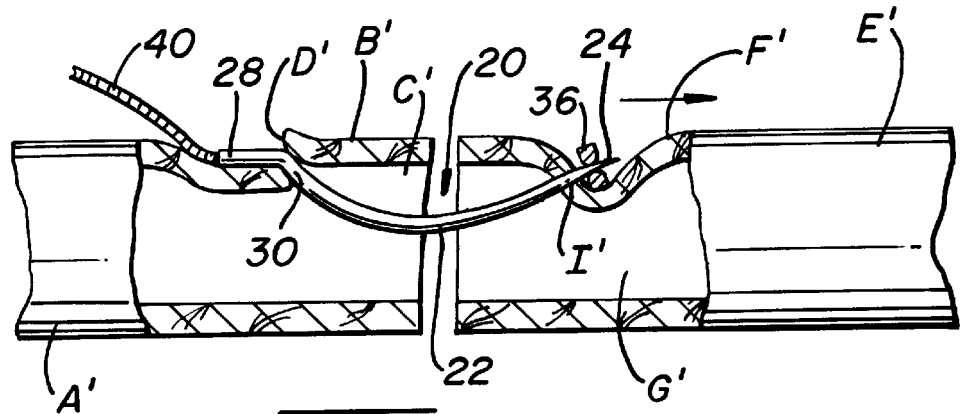
FIG. 13 is a view similar to FIG. 12 illustrating the surgical needle of FIG. 2 being drawn partially through the first vascular tissue section.

Referring now to FIG. 13, as pointed tip 24 is grasped by needle holder 36 and moved substantially longitudinally parallel to second vascular tissue section E', shank 28 is atraumatically drawn through entrance hole D' in first vascular tissue section A'. This is facilitated by the juncture angle a which enables shank 28 to easily slide through entrance D' as pointed tip 24 is pulled parallel to the longitudinal axis of second vascular tissue section E'. More importantly, it has been found that by forming juncture angle a with an optimal angle of about 45°, shank 28 easily and atraumatically slips through entrance hole D'.

As shown in FIG. 14, once shank 28 has been drawn through entrance hole D', length of suture material 40 passes through entrance hole D'. Continued pulling of pointed tip 24 by needle holder 36 parallel to second vascular tissue section E' thereby draws length of suture material 40 into and through lumens C' and G'.

To draw surgical needle 20 out of lumen G' in second vascular tissue E', surgical needle 20 is drawn parallel to second vascular tissue section E' as shown in FIG. 15. Again, juncture angle a enables shank 28 to easily slip through exit hole I'with minimal trauma thereto. As specifically shown, the height "H" of the space adjacent vascular tissue section E' is significantly less than that of height h illustrated in FIG. 10 with respect to prior art surgical needle 10 hereinabove.

FIGS. 15 and 16 illustrate, in side-by-side comparison, the significant differences in operating space required adjacent vascular tissue sections E, E' in order to manipulate prior art surgical needle 10 and novel surgical needle 20.

It will be understood that various modifications may be made to the embodiments disclosed herein. For example, the surgical needle may have a varying or constant radius of curvature as well as a straight or an arcuate shank. Additionally, alternate methods of suture attachment are also contemplated. Therefore, the above description should not be construed as limiting, but merely as exemplifications of preferred embodiments. Those skilled in the art will envision other modifications within the scope and spirit of the claims appended hereto.

What is claimed is:

1. A surgical suturing needle comprising:

an arcuate body having a pointed tip at one end thereof; and a relatively straight shank formed adjacent an opposite end, the juncture of the shank and the arcuate body forming an immediate abrupt angle in a range of about 30° to about 70° therebetween, the arcuate body being measured from the immediate abrupt angle to the pointed tip wherein a radius of curvature of the arcuate body progressively increases form the juncture with the shank to the pointed tip.

2. The surgical suturing needle as recited in claim 1, wherein the abrupt angle is an acute angle.

3. The surgical suturing needle as recited in claim 1, wherein the abrupt angle is approximately 45°.

4. The surgical suturing needle as recited in claim 1, wherein the length of the shank is less than the radius of the arcuate body.

5. The surgical suturing needle as recited in claim 1, wherein the length of the shank is approximately 10–45% of the overall length of the surgical suturing needle.

6. The surgical suturing needle as recited in claim 1, wherein the length of the shank is approximately 0.05 to 0.15 inches.

7. The surgical suturing needle as recited in claim 1, wherein a portion of the arcuate body has relatively flat sides.

8. The surgical needle as recited in claim 1, wherein the shank has a substantially circular cross-section.

9. The surgical suturing needle as recited in claim 1, further comprising suture attachment structure formed in the shank.

10. A surgical suturing needle comprising:

an arcuate body having a pointed tip at a first end, the arcuate body having a radius of curvature which progressively increases from a second end of the arcuate body to the pointed tip; and a relatively straight shank formed adjacent the second end and having a bore therein for receipt of an end of a length of suture material, wherein a juncture of the shank and the arcuate body defines an abrupt angle in a range of about 30° to about 70°.

11. The surgical suturing needle as recited in claim 10, wherein the abrupt angle is approximately 45°.

\* \* \* \* \*

UNITED STATES PATENT AND TRADEMARK OFFICE
CERTIFICATE OF CORRECTION

PATENT NO. : 5,891,164
DATED : April 6, 1999
INVENTOR(S) : Dabir et al.

It is certified that error appears in the above-identified patent and that said Letters Patent is hereby corrected as shown below:

On the cover page of the patent, after the listing of inventors please insert the following:

[73] Assignee: United States Surgical Corporation.
     Norwalk, Conn.

Signed and Sealed this

Twenty-second Day of May, 2001

Attest:

NICHOLAS P. GODICI

*Attesting Officer*    *Acting Director of the United States Patent and Trademark Office*